(12) United States Patent
Weltzin et al.

(10) Patent No.: US 7,645,456 B2
(45) Date of Patent: *Jan. 12, 2010

(54) VACCINIA VIRUS STRAINS

(75) Inventors: Richard A. Weltzin, Lunenburg, MA (US); Thomas P. Monath, Harvard, MA (US)

(73) Assignee: Sanofi Pasteur Biologics Co., Cambridge, MA (US)

(*) Notice: Subject to any disclaimer, the term of this patent is extended or adjusted under 35 U.S.C. 154(b) by 628 days.

This patent is subject to a terminal disclaimer.

(21) Appl. No.: 10/826,680

(22) Filed: Apr. 16, 2004

(65) Prior Publication Data

US 2009/0169512 A1   Jul. 2, 2009

Related U.S. Application Data

(63) Continuation-in-part of application No. 10/445,671, filed on May 27, 2003, now Pat. No. 7,115,270, which is a continuation of application No. 09/840,751, filed on Apr. 23, 2001, now Pat. No. 6,723,325.

(51) Int. Cl.
*A61K 39/275* (2006.01)
*C12N 1/00* (2006.01)
*A61K 39/285* (2006.01)

(52) U.S. Cl. .................. 424/232.1; 435/235.1

(58) Field of Classification Search .......... None
See application file for complete search history.

(56) References Cited

U.S. PATENT DOCUMENTS 4,315,914 A    2/1982  Arakawa et al.
4,567,147 A    1/1986  Ooi et al.
5,656,465 A    8/1997  Panicali et al.
6,723,325 B1 *  4/2004  Weltzin et al. .......... 424/323.1
7,115,270 B2 * 10/2006  Weltzin et al. .......... 424/232.1

FOREIGN PATENT DOCUMENTS

DE        2 145 477          3/1973
EP        0 157 528          10/1985
WO        WO 02/085411 A1    10/2002

OTHER PUBLICATIONS

Dumbell, K. and M. Richardson, Virological investigations of specimens from buffaloes affected by buffalopox in Maharashtra State, India between 1985 and 1987. Arch Virol (1993) 128:257-267.*

Singh, et al., Comarative sequence analysis of envelope protein genes of Indian buffalopox virus isolates. Arch Virol (2006) 151:1995-2005.*

Tartaglia, et al., Live Vectors as Vaccines: Highly Attenuated Poxvirus Vectors. AIDS Research and Human Retroviruses. 1992; vol. 8, No. 8:1445-7.*

(Continued)

*Primary Examiner*—Bruce R. Campell
*Assistant Examiner*—Stuart W Snyder
(74) *Attorney, Agent, or Firm*—Clark & Elbing LLP (57) ABSTRACT

The invention provides attenuated vaccinia virus vaccines that can be used in methods to prevent or treat small pox in patients, as well as methods of obtaining such vaccines.

2 Claims, 5 Drawing Sheets

OTHER PUBLICATIONS

Kutinova, et al. Search for optimal parent for recombinant vaccinia virus vaccines. Study of three vaccinia virus vaccinal strains and several virus lines derived from them. Vaccine, ,1995; vol. 13. No. 5, pp. 487-493.*

Buller, et al. Deletion of the vaccinia virus growth factor gene reduces virus virulence. Journal of virology (United States) Mar. 1988, 62 (3) p. 866-74.*

Šroller, et al. Effect of 3-b-hydroxysteroid dehydrogenase gene deletion on virulence and immunogenicity of different vaccinia viruses and their recombinants. Arch Virol (1998) 143: 1311-1320.*

Rosengard, et al. Variola virus immune evasion design: expression of a highly efficient inhibitor of human complement. PNAS Jun. 25, 2002 , 99 (13) p. 8808-13.*

Dunlop, et al. Variola virus immune evasion proteins. Microbes and infection / Institut Pasteur ( France ) Sep. 2003, 5 (11) p. 1049-56.*

Kim, et al. Evidence that vaccinia virulence factor ER binds to Z-DNA in vivo: Implications for development of a therapy for poxvirus infection. PNAS. 2004, V 101, N6 ( FEB 10 ), p. 1514-1518.*

Abrahams, et al. The vaccinia virus N1L ORF may encode a multifunctional protein possibly targeting different kinases, one of which influences ATP levels in vivo. Annals of the New York Academy of Sciences (United States) Nov. 2005, 1056 p. 87-99.*

Cooray, et al. Functional and structural studies of the vaccinia virus virulence factor N1 reveal a Bcl-2-like anti-apoptotic protein. Journal of general virology (England) Jun. 2007, 88 (Pt 6) p. 1656-66.*

Osborne, et al. Genomic differences of vaccinia virus clones from Dryvax smallpox vaccine: The Dryvax-like ACAM2000 and the mouse neurovirulent Clone-3. Vaccine. 2007.*

Dumbell, K. and M. Richardson, Virological investigations of specimens from buffaloes affected by buffalopox in Maharashtra State, India between 1985 and 1987. Arch Virol (1993) 128:257-267.*

Singh, et al., Comarative sequence analysis of envelope protein genes of Indian buffalopox virus isolates. Arch Virol (2006) 151:1995-2005.*

Halstead et al., "Selection of Attenuated Dengue 4 Viruses by Serial Passage in Primary Kidney Cells," Am. J. Trop. Med. Hyg. 33(4):666-671, 1984.

Henderson et al., "Consensus Statement: Smallpox as a Biological Weapon. Medical and Public Health Management," JAMA 281:2127-2137, 1999.

Jennings et al., "Virus Vaccines," In: Virus Culture, a Practical Approach, ed. A.J. Cann, Oxford University Press, New York 149-182, 1999.

Kutinova et al., "Search for Optimal Parent for Recombinant Vaccinia Virus Vaccines. Study of Three Vaccinia Virus Vaccinal Strains and Several Virus lines Derived from them," Vaccine 13:487-493, 1995.

Kutinova et al., "Influence of the Parental Virus Strain on the Virulence and Immunogenicity of Recombinant Vaccinia Viruses Expressing HBV preS2-S Protein or VZV Glycoprotein I," Vaccine 14:1045-1052, 1996.

Lee et al., "Molecular Attention of Vaccinia Virus: Mutant Generation and Animal Characterization," Journal of Virology 66:2617-2630, 1992.

LeDuc et al., "Current Status of Smallpox Vaccine," Emerging Infectious Diseases 5:593, 1999.

Liprandi, "Isolation of Plaque Variants Differing in Virulence from the 17D Strain of Yellow Fever Virus," J. gen. Virol 56:363-370, 1981.

Marchevsky et al., "Phenotypic Analysis of Yellow Fever Virus Derived from Complementary DNA," The American Society of Viral Medicine and Hygiene 5200:75-80, 1995.

Weltzin et al., "Clonal Vaccinia Virus Grown in Cell Culture as a New Smallpox Vaccine," Nature Medicine 9:1125-1130, 2003.

Weltzin et al., U.S. Appl. No. 10/445,671, filed May 27, 2003.

Goebel et al., "The Complete DNA Sequence of Vaccinia Virus," Virology 179:247-266, 1990.

Plotke et al., "Comparative Results of Smallpox Revaccination Using Regular and Dry Smallpox Vaccine (DryVax)," Illinois Medical Journal 125:140-141, 1964.

International Preliminary Report on Patentability from International Application No. PCT/US2005/012947.

* cited by examiner

Experiment 2

VACCINIA VIRUS STRAINS

CROSS REFERENCE TO RELATED APPLICATIONS

This application is a continuation-in-part of, and claims priority from, U.S. Ser. No. 10/445,671, filed May 27, 2003 now U.S. Pat. No. 7,115,270, which is a continuation of U.S. Ser. No. 09/840,751, filed Apr. 23, 2001 now U.S. Pat. No. 6,723,325. Each of the prior applications is incorporated herein by reference.

This invention was made with Government support under Grant No. 1N01AI000071-001 awarded by National Institute of Allergy and Infectious Diseases. The Government has certain rights in this invention.

BACKGROUND OF THE INVENTION

This invention relates to vaccinia virus strains, compositions including the strains, and methods employing the strains.

Variola virus, the causative agent of smallpox, is a member of the Orthopoxvirus genus, which also includes monkeypox, cowpox, and vaccinia viruses. The disease caused by variola major strains is characterized by a low infectious dose (10-100 virions), a long incubation period (averaging 12 days), fever, constitutional symptoms, rash progressing to a pustular stage, death in up to 30% of those affected, and scarring in survivors. The disease is spread person-to-person via the respiratory route by contact (droplets) and, possibly, by aerosol.

Smallpox was one of the most important causes of morbidity and mortality worldwide throughout the first half of the $20^{th}$ century. However, in part because of the lack of an animal reservoir for the virus, the systematic use of a vaccine (live, attenuated vaccinia virus) was highly effective in fighting this disease. Indeed, between 1967-1977, a global program of smallpox eradication resulted in the elimination of the natural disease (Fenner et al., WHO, Geneva, p. 1460, 1988). Because of the absence of smallpox and the risk of vaccine-associated adverse events, routine vaccination of children, hospital personnel, and military personnel was ceased, leaving only persons working with vaccinia and related viruses in the laboratory being immunized. Thus, a substantial portion of the world's population has no immunity to smallpox. The remaining population has little residual immunity, as vaccine immunity lasts only 5 years after primary vaccination and less than 20 years after revaccination. The eradication of smallpox and the cessation of vaccination have, thus, created vulnerability in the population to covert attack or biowarfare employing variola virus. Should such an event occur, epidemic spread would be unchecked by an immune barrier in the population (Anon. (Editorial), Lancet 353:1539, 1999; Henderson, Science 283:1279-1282, 1999; Henderson et al., J.A.M.A. 281:2127-2137, 1999).

Because of the uncertainties surrounding the smallpox eradication, vaccine was stockpiled for emergency use. In the United States, for example, 155,000 vaccine vials (nominally 15.5 million doses) produced by Wyeth Laboratories were originally stockpiled under the control of the Centers for Disease Control and Prevention (CDC), Atlanta, Ga. At a meeting of the National Vaccines Advisory Committee in January 1999, the CDC reported on the status of the national smallpox vaccine repository. At that time, of the 15.5 million doses held by Wyeth, 3.4 million doses had failed quality control testing and 10.3 million were beyond the expiration date specified by the last control test for extended dating, leaving 1.7 million doses that met release specifications (LeDuc, Presentation to the National Vaccines Advisory Committee, Washington D.C., Jan. 11-12, 1999). In addition to the limited supply, the vaccine is packaged in 100 dose vials, which restricts distribution and increases the likelihood of wastage during an emergency.

In addition to the U.S. stockpile, there is a supply of vaccine (Lister, Elstree strain) stored at the National Institute of Public Health, Bilthoven, Netherlands, and certain other countries have supplies of smallpox vaccine, which at the time of eradication may have included up to 300 million doses. However, similar problems of stability in storage have reduced this supply to less than 50 million doses (Henderson, Science 283:1279-1282, 1999).

SUMMARY OF THE INVENTION

The invention provides stable strains of vaccinia virus that are isolated from cultured cells in which Dryvax® has been propagated, and which have characteristics that make them suitable for use as human vaccines against smallpox. The invention also provides methods of generating these strains and methods of using them to prevent and treat smallpox infection and disease.

Accordingly, in a first aspect, the invention provides a clonal strain of attenuated vaccinia virus that is isolated from cultured cells in which Dryvax®, ACAM1000, ACAM2000, or a variant thereof (see below) has been cultured and, when administered to a human in an amount effective to induce a protective or therapeutic immune response against variola virus in the human, is acceptably attenuated in the human.

The clonal strains can have, for example, substantially the same virulence and/or immunogenicity as Dryvax®. Preferably, the vaccinia virus is produced in substantially the same or greater amounts as Dryvax® when inoculated into cell cultures, and/or has substantially the same digestion pattern as Dryvax® when digested with a restriction endonuclease.

The clonal strain can also have, for example, substantially the same virulence and/or immunogenicity as vaccinia virus strain ACAM1000 or ACAM2000 (deposited as ATCC Deposit No. PTA-3321 on Apr. 19, 2001; see clone 2, below) when tested in appropriate animal models or in humans. The vaccinia virus also be produced in substantially the same or greater amounts as vaccinia virus strain ACAM1000 or ACAM2000 when inoculated into cell cultures, and/or has substantially the same digestion pattern as vaccinia virus strain ACAM1000 or ACAM2000 when digested with a restriction endonuclease. ACAM1000 and ACAM2000 have been found to have the same sequences, but have been given different designations to reflect the cell cultures in which they are typically propagated (ACAM1000-MRC5 cells; ACAM2000-Vero cells).

In a second aspect, the invention provides a pharmaceutical composition including a clonal strain of vaccinia virus, as described above and elsewhere herein, and a pharmaceutically acceptable carrier or diluent.

In a third aspect, the invention provides a method of preventing or treating variola virus infection in a patient by administering such a pharmaceutical composition to the patient. The pharmaceutical composition can be administered to the patient by, for example, scarification, in an amount ranging from, for example, $1 \times 10^4$ to $1 \times 10^6$ plaque-forming units.

In a fourth aspect, the invention provides a method of obtaining a clonal strain of attenuated vaccinia virus for use as a vaccine. This method involves (i) propagating Dryvax® or another vaccinia strain as described herein (e.g., ACAM1000 or ACAM2000) in a cell culture system, and (ii) isolating from the cell culture system a clonal strain of vaccinia virus that has substantially the same virulence, immunogenicity, growth characteristics in culture, or restriction endonuclease digestion pattern as Dryvax®, vaccinia virus strain ACAM1000, or vaccinia virus strain ACAM2000. The virulence of the vaccinia virus can be tested in this method by, for example, a rabbit skin test or a suckling mouse neurovirulence test. Growth characteristics in culture can be determined using, e.g., human diploid (MRC-5) cells or Vero cells. Preferably, the vaccinia virus identified using this method, when administered to a human in an amount effective to induce a protective or therapeutic immune response against variola virus in the human, is acceptably avirulent in the human.

In a fifth aspect, the invention includes clonal strains of attenutated vaccinia virus that have nucleotide sequences that are substantially identical to the sequence of SEQ ID NO: 1 or SEQ ID NO:2. The nucleotide sequence can be, e.g., at least 70%, 80%, 90%, 95%, or 98% identical to the sequence of SEQ ID NO: 1 or SEQ ID NO:2 (also see below).

In a sixth aspect, the invention includes clonal strains of attenutated vaccinia viruses that have nucleotide sequences that hybridize to the sequence of SEQ ID NO: 1 or SEQ ID NO:2, a fragment of SEQ ID NO: 1 or SEQ ID NO:2, or the complement of SEQ ID NO: 1 or SEQ ID NO:2, under highly stringent conditions. The fragment can include, for example, a coding sequence selected from the group consisting of SEQ ID NOs:3-471 (odd numbers), or the complement thereof.

In a seventh aspect, the invention provides clonal strains of attenuated vaccinia virus that have nucleotide sequences that encode a polypeptide selected from the group consisting of SEQ ID NOs:4-472 (even numbers).

Further, in an eighth aspect, the invention provides clonal strains of attenuated vaccinia viruses that include one or up to 235 polypeptides having amino acid sequences that are substantially identical to those encoded by the sequences of SEQ ID NOs: 1 or 2, or the complements thereof. For example, the clonal strains can include 235 polypeptides having amino acid sequences that are substantially identical to those encoded by the sequences of SEQ ID NOs: 1 or 2, or the complements thereof.

A polynucleotide of the invention hybridizes, preferably under stringent conditions, to a polynucleotide having a sequence as shown in the sequence listing (SEQ ID NOs: 1 or 2, odd numbers of SEQ ID NOs:3-471, or the complements thereof). Hybridization procedures are described, e.g., by Ausubel et al. (Current Protocols in Molecular Biology, John Wiley & Sons, New York, N.Y., 1998), Silhavy et al. (Experiments with Gene Fusions, Cold Spring Harbor Laboratory Press, Cold Spring Harbor, N.Y., 1984), and Davis et al. (A Manual for Genetic Engineering: Advanced Bacterial Genetics, Cold Spring Harbor Laboratory Press, Cold Spring Harbor, N.Y., 1980).

Important parameters that can be considered for optimizing hybridization conditions are reflected in the following formula, which facilitates calculation of the melting temperature (Tm), which is the temperature above which two complementary DNA strands separate from one another (Casey et al., Nucl. Acid Res. 4:1539, 1977): Tm=81.5+0.5×(% G+C)+1.6 log (positive ion concentration)−0.6×(% formamide). Under appropriate stringency conditions, hybridization temperature (Th) is approximately 20 to 40° C., 20 to 25° C., or, preferably, 30 to 40° C. below the calculated Tm. Those skilled in the art will understand that optimal temperature and salt conditions can be readily determined empirically in preliminary experiments using conventional procedures. For example, stringent conditions can be achieved, both for pre-hybridizing and hybridizing incubations, (i) within 4-16 hours at 42° C., in 6×SSC containing 50% formamide or (ii) within 4-16 hours at 65° C. in an aqueous 6×SSC solution (1 M NaCl, 0.1 M sodium citrate (pH 7.0)). For polynucleotides containing 30 to 600 nucleotides, the above formula is used and then is corrected by subtracting (600/polynucleotide size in base pairs). Stringent conditions are defined by a Th that is 5 to 10° C. below Tm.

In another example, high stringency conditions can be defined as conditions that allow hybridization comparable with the hybridization that occurs using a DNA probe of at least 100, e.g., 200, 350, or 500, nucleotides in length, in a buffer containing 0.5 M NaHPO$_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Additional information concerning high stringency conditions can be found, for example, in Ausubel et al. (supra).

By "polypeptide" or "protein" is meant any chain of amino acids, regardless of length or post-translational modification (e.g., glycosylation or phosphorylation). Both terms are used interchangeably in the present application.

By "homologous amino acid sequence" is meant an amino acid sequence that differs from an amino acid sequence shown in the sequence listing (even numbers, SEQ ID NOs: 4-472) or sequence appendices, or an amino acid sequence encoded by a nucleotide sequence shown in the sequence listing (odd numbers, SEQ ID NOs:3-471) or sequence appendices, by one or more (e.g., 1-200, 5-150, 10-100, 25-75, or 50-60) non-conservative amino acid substitutions, deletions, or additions. Such a sequence can be, for example, at least 75%, 80%, 90%, 95%, 97%, 98%, or 99% identical to an amino acid sequence shown in the sequence listing (even numbers, SEQ ID NOs:4-472) or sequence appendices. The invention includes clonal strains of attenuated vaccinia viruses that include one or up to 235 proteins having amino acid sequences that are homologous with the amino acid sequences of the sequence listing or sequence appendices.

Homologous amino acid sequences include sequences that are identical or substantially identical to an amino acid sequence as shown in the sequence listing (even numbers, SEQ ID NOs:4-472) or sequence appendices. By "amino acid sequence that is substantially identical" is meant, for example, a sequence that is at least 80%, 90%, 95%, 97%, or 99% identical to an amino acid sequence of reference and that differs from the sequence of reference, if at all, by a majority of conservative amino acid substitutions.

Conservative amino acid substitutions typically include substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology can be measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Homologous polynucleotide sequences are defined in a similar way. For example, a homologous sequence can be one that is at least 55%, 60%, 75%, 85%, 90%, 95%, 97%, 98%, or 99% identical to a sequences of any of the nucleotide sequences set forth in the sequence listing (SEQ ID NOs: 1 and 2; odd numbers of SEQ ID NOs:3-471) or sequence appendices (also see below).

The invention provides several advantages. For example, previously, smallpox vaccine was produced by inoculation of vaccinia virus into the skin of calves, followed by scraping of the skin of the calves to harvest live virus. The crude virus preparation obtained underwent minimal purification before use in vaccinating human recipients, leaving open the possibility of pathogen contamination. The vaccines of the present invention are produced in a cell culture system that is acceptable by modem standards for vaccine manufacture and is highly purified, thus eliminating this problem. An additional advantage of using cloned viruses, such as those of the present invention, is that the characteristics of such viruses are unlikely to change during propagation and vaccine manufacturing, as compared to mixed populations of viruses. Indeed, we have shown that a virus according to the invention maintains its phenotype under repeated passage and expansion in cell culture, is free from contaminants, and is capable of being produced in cell culture in amounts suitable for large-scale vaccine manufacture.

Other features and advantages of the invention will be apparent from the following detailed description, the drawings, and the claims.

DETAILED DESCRIPTION

The invention provides clonal strains of attenuated vaccinia viruses that can be used in vaccination methods against smallpox (i.e., variola virus). As is described further below, the attenuated vaccinia strains of the invention can be obtained by isolating vaccinia clones from cell cultures in which Dryvax®, ACAM1000, or ACAM2000 has been propagated. The invention also provides methods of using vaccines that include these vaccinia viruses in the prevention or treatment of smallpox, as well as methods of obtaining such clonal strains of vaccinia viruses.

The vaccines of the invention are derived from, and have similar characteristics to, Dryvax® (New York City Board of Health strain, Wyeth Laboratories), which is currently licensed by the U.S. Food and Drug Administration (FDA) and consists of a mixed population of vaccinia viruses generated in calf skin. The vaccines must have acceptably attenuated virulence for humans who are vaccinated with them. An acceptable level of attenuation can be, for example, a level that is similar to (e.g., does not differ in a statistically significant manner from) that observed with Dryvax®, and can be determined using any of the in vitro or in vivo tests described below. A property of vaccinia virus is its neurotropism, or ability to replicate in cells of the central nervous system, causing inflammation (i.e., encephalitis). Preferably, the vaccines of the invention are not more neurotropic than Dryvax® and do not cause postvaccinal encephalitis in treated patients.

The vaccines and methods of the present invention are described further below.

Indications for Use

The principal indication for use of the vaccines of the invention is in the prevention of smallpox in populations exposed or potentially exposed to smallpox after an act of bioterrorism or biowarfare. Efficacy of the vaccines of the invention advantageously is high (>95%), and the vaccines protect against both person-person spread of the virus and primary exposure to high-dose aerosol exposure to biological weapons. Given this principal indication, the vaccines of the invention can be used, for example, to create a new national stockpile of smallpox (vaccinia) vaccine, and manufacture can be continued annually to maintain a continuous stock of in-date vaccine for an extended period of time.

The vaccines are not necessarily intended for routine use, except in laboratory workers who are exposed to vaccinia, cowpox, monkey pox, variola, or other members of the Orthopoxvirus genus. Otherwise, the vaccines are to be released under emergency conditions, as determined by the national security and public health authorities. Under the circumstances of such an emergency, the risks of adverse events associated with vaccinia would be outweighed by the potential benefits of protecting individuals against smallpox and society against spread of the disease. It is recognized that emergency use of the vaccines may be difficult to control, that infants, who are at higher risk of postvaccinal encephalitis, will receive the vaccines, and that precautions and contraindications for use in persons with underlying conditions (e.g., history of eczema, pregnancy, and immunosuppression) may be ignored. For these reasons, it is important that the cell culture-derived vaccines of the invention are not more virulent than the currently licensed product.

Depending upon events that cannot be accurately predicted, there may be a decision to undertake pre-exposure prophylaxis of certain groups, including military personnel, civilian medical personnel, and so-called 'first responders.' The inherent safety profile of the vaccines in these groups, while of great importance, is enhanced by deliberate application of the product and avoidance of use in individuals with risk factors for adverse events. Under these circumstances, the principal risks are autoinoculation, ocular vaccinia, and accidental infection, all of which are self-limited adverse events. There is a small risk of accidental infection of others with underlying risk factors.

Of course, should circumstances in the country or world change such that routine vaccination of additional members of the population (e.g., children), or even the entire population, is thought to be desirable, the vaccines of the present invention can be used for these purposes as well.

Modes and Amounts of Administration

The vaccines of the invention are prepared by propagation of a desired strain of vaccinia virus (e.g., strain ACAM1000, ACAM2000, or a variant thereof; ATCC Deposit No. PTA-3321; see below) in a cell culture system, and purification of the cultured strain from the system using standard methods. For example, the strain can be cultured in diploid human lung fibroblast cells, such as MRC-5 cells, primary chick embryo fibroblast cells, Vero cells, or any other appropriate cell type, as can be determined by those of skill in this art. The culture can take place using any appropriate system such as, for example, the Nunc Cell Factory®.

Purified virus can be lyophilized for later use or can be immediately prepared in a pharmaceutical solution. Numerous pharmaceutically acceptable solutions for use in vaccine preparation are well known in the art and can readily be adapted for use in the present invention by those of skill in this art. (See, e.g., Remington's Pharmaceutical Sciences (18$^{th}$ edition), ed. A. Gennaro, 1990, Mack Publishing Co., Easton, Pa.) However, the viruses can simply be diluted in a physiologically acceptable solution, such as sterile saline or sterile buffered saline, with or without an adjuvant or carrier. Optionally, the pharmaceutical solution can contain a component that provides viscosity (e.g., glycerol) and/or a component that has bactericidal properties (e.g., phenol). The vaccines can be stored at a concentration of $10^7$-$10^9$ plaque-forming units (PFU)/ml, for example, $10^8$ PFU/ml.

The vaccines of the invention can be administered to patients by, for example, scarification, using standard methods. For example, a bifurcated needle can be used in such an approach. Alternatively, the vaccine can be administered using any other standard route that is found to be acceptable by those of skill in this art. For example, the vaccine can be administered by subcutaneous or intradermal injection, or by another parenteral route, such as by intramuscular injection. The amount of vaccine administered to an average-sized adult can be, for example, $1 \times 10^4$ to $1 \times 10^6$ plaque-forming units. As a specific example, $2.5 \times 10^5$ plaque-forming units can be used.

Preferably, vaccination is carried out before any exposure to variola, but vaccination can also be carried out with patients who have been exposed to variola, preferably within a few days of the exposure. Vaccination can be carried out only once in a person's lifetime or can be repeated after a period of time, such as several years (e.g., 5-10 years), as determined to be appropriate by those of skill in this art.

Identification of Vaccine Candidates

The invention also includes methods of identifying vaccinia vaccine candidates. These candidates can be identified by isolating clonal strains from cell cultures inoculated with Dryvax®, and characterizing these clones using any of the in vitro or in vivo methods described below. For example, a candidate vaccine strain can be compared with Dryvax® for plaque size, yield in cell culture (using, e.g., MRC-5 or Vero cells), rabbit cutaneous virulence, suckling mouse neurovirulence, monkey neurovirulence, or protection in a mouse challenge model. Preferred candidates are those with virulence that is similar to or less than that of Dryvax®, which induce protective immunity that is similar to or greater than that of Dryvax®, and also have growth characteristics that are similar to or greater than those of Dryvax®. Candidates that are variants of ACAM1000 or ACAM2000 can also be tested.

Prior to the present invention, isolation of a clonal strain that has satisfactory characteristics of a vaccine candidate was unpredictable, because the long history of passage of vaccinia has resulted in the generation of multiple subpopulations of variants (i.e., a genetic swarm), with potentially different biological properties. It was also uncertain whether a single variant, isolated by plaque purification (i.e., biological cloning) would have the same phenotypic characteristics as the sum of the multiple variants in the original mixed virus population. In fact, prior to the present invention, it would have been surprising if this were the case. Based on the present invention, it is now known for the first time that clonal isolates of Dryvax® can be effective.

Development and preclinical characterization of vaccines of the invention is described further, as follows.

Development and Preclinical Characterization of Vaccinia Vaccines

As is discussed above, Dryvax® is the vaccinia vaccine that is currently licensed by the FDA, was derived from the New York City Board of Health (NYCBH) strain, and was produced up to 1982 by Wyeth-Lederle by the bovine calf lymph method (also see ATCC Deposit No. VR-325). Dryvax® consists of a live, attenuated vaccinia virus and does not exist as a cell culture product. We adapted the smallpox vaccine strain of vaccinia virus for propagation under controlled conditions in laboratory-grown cultures of human lung fibroblast cells so that modern techniques could be used for vaccine production. To develop a cell culture vaccine, we had to separate Dryvax® from potential adventitious viral contaminants by passage at terminal dilution, and we did this with and without cloning, as is discussed further below. From the mixture of variants (the genetic swarm) in Dryvax®, we selected candidate vaccines that have similar biological characteristics in animals and genomic similarity to the licensed vaccine, providing a high degree of certainty that they are as effective clinically as the original calf lymph product.

In one strategy used for adaptation, the vaccinia virus was cloned to isolate the virus from possible contaminating microorganisms derived from calf skin. Through use of this strategy, six clones were isolated. The cloned viruses exhibited a variety of characteristics with greater or lesser virulence when compared to Dryvax®. Surprisingly, given the expected mixture of variants in Dryvax®, three clones were found to be similar to Dryvax® in virulence tests in animals and differed primarily in growth rate in cell culture. Any of these strains, as well as others with similar characteristics, can be used in smallpox vaccination methods, according to the invention.

In another strategy, the virus was not cloned, with the expectation that virus derived by this method would be more likely to behave like the strain from which it was derived. Surprisingly, we found, however, that the strain produced without cloning, while behaving similarly to Dryvax® in in vitro tests, did not have the characteristics of the vaccine strain, but in fact was more virulent when tested in laboratory animals. Thus, we focused our development efforts on cloned viruses with characteristics similar to those of the Dryvax® vaccine strain. The details of our characterization are as follows.

Dryvax® was inoculated into cultures of MRC-5 cells and six clones of vaccinia virus were obtained by plaque-purification. Each clone was recloned twice to ensure clonality and freedom from contaminants. Dryvax® was also inoculated into MRC-5 cell cultures at a multiplicity of infection (MOI) of 0.001 PFU per cell to derive an uncloned (polyclonal) virus preparation. This virus was subsequently passed in MRC-5 cells twice more at low MOI. All six clones and the polyclonal preparation were tested in an extensive series of comparative analyses along side Dryvax® for in vitro and in vivo characteristics. In particular, each clone and the polyclonal preparation were analyzed for plaque morphology, yield in MRC-5 cells, restriction endonuclease mapping patterns, the formation of cutaneous pocks in rabbits, and mouse neurovirulence. A subset of clones was further tested for induction of protective immunity in mice. The objective was to select a vaccine strain from the Dryvax® pool with biological similarity to Dryvax®. Table 1 summarizes the results of these studies.

TABLE 1

Characterization of 7 vaccinia virus candidates

Results (relative to Dryvax ® for qualitative assays)

| Test | Dryvax ® | Clone 1 | Clone 2 | Clone 3 | Clone 4 | Clone 5 | Clone 6 | Poly |
|---|---|---|---|---|---|---|---|---|
| Plaque size (mean, mm) | 0.42 | 0.43 | 0.49 | 0.36 | 0.65 | 0.25 | 0.27 | 0.46 |
| Yield in MRC-5[†] | 4.0 | 13.5 | 7.0 | 10.6 | 15.6 | 4.7 | 1.5 | 7.0 |
| RE analysis | | Same | Same | Same | Same | Same | Same | Same |
| Rabbit skin test | | High | Same | High | Same | High | Same | High |
| Suckling mouse neurovirulence | | High | Same | High | Same | High | Same | High |
| Immunogenicity in mice | | Not tested | Same | Same | Same | Not tested | Not tested | Not tested |

[†]pfu/ml × $10^6$

From these studies, clones 2 and 4 were identified as having characteristics which show that these clones are suitable for use as a new smallpox vaccine. Clone 6 also has suitable characteristics, but does not grow as well as clones 2 and 4 in culture.

Suckling Mouse Neurovirulence

Adult mice were determined to be insusceptible to intracranial (IC) inoculation of unmodified Dryvax®. A test in suckling mice was therefore developed. Suckling mice (3-4 days old) were injected with tenfold dilutions of virus and survival time was determined. Three experiments were conducted, with Dryvax® tested in each as a standard. We observed that suckling mice inoculated IC with Dryvax® uniformly developed fatal encephalitis with an $LD_{50}$ of ~1.0 $log_{10}$ PFU and a mean time to death of seven days. This test was thus determined to be useful for comparing neurovirulence of vaccine candidates with parental Dryvax®. The results of these experiments are summarized in Table 2, and the number of mice surviving and the average survival times found in this analysis are shown in FIGS. 1A-1D.

TABLE 2

Neurovirulence for suckling mice, vaccinia vaccine candidates

| | | Parameter | | | |
|---|---|---|---|---|---|
| Experiment | Virus | $LD_{50}$[1] | $LD_{90}$[1] | AST[2] | (SD) |
| 1 | Dryvax ® | 1.68 | 3.03 | 7.78 | (4.19) |
| | Polyclonal | <1.3 | 1.94 | 6.09 | (1.14) |
| | Clone 1 | <2.3 | <2.3 | 4.20 | (1.03) |
| 2 | Dryvax ® | 1.3 | 2.1 | 6.67 | (0.71) |
| | Clone 2 | 1.55 | 2.25 | 6.80 | (2.74) |
| | Clone 3 | <1.3 | <1.3 | 5.00 | (1.16) |
| | Clone 4 | 2.59 | 3.16 | 6.11 | (1.36) |
| 3 | Dryvax ® | 2.4 | 4.15 | 8.64 | (3.42) |
| | Clone 5 | <1.3 | <1.3 | 4.08 | (1.08) |
| | Clone 6 | 1.57 | 2.47 | 7.73 | (4.63) |

[1]50% intracerebral lethal dose per 0.02 mL inoculum on day 10 after infection
[1]90% intracerebral lethal dose per 0.02 mL inoculum on day 10 after infection
[2]Average survival time, days (standard deviation) at ~10-100 $LD_{50}$ Additional tests can be used to test the virulence of vaccine candidates. For example, we developed a rabbit cutaneous virulence test. This test was successfully developed using intradermal inoculation of unpassaged Dryvax®, which produced dose-related pock lesions characterized by erythema, induration, and in some cases a central lesion. As another example, a monkey neurovirulence test can be used. In this test, a cloned Dryvax®-derived candidate is tested against Dryvax® by IC inoculation of graded virus doses.

We also developed a mouse challenge model for protection tests. In this model, the WR strain of vaccinia was used to challenge 6-8 week-old mice by the intranasal (IN) route. The $LD_{50}$ is ~4.5 $log_{10}$ PFU and the mean time to death is 6-7 days after challenge. The test is sufficiently robust to use in pre-clinical protection studies with the new vaccine candidate. Similar models using other Orthopoxviruses, such as cowpox virus, can also be used.

The ability of Dryvax® and clones 2 and 4 to induce protective immunity against vaccinia WR challenge in mice was tested. Clone 3 was also tested to determine whether a clone with greater virulence also induces a greater immune response. Four-week-old mice were immunized with graded doses of each virus strain. The virus was inoculated into the skin by scarification with a bifurcated needle, which is the method used to inoculate Dryvax® in humans. Three weeks after immunization, the mice were challenged with 6.5 $log_{10}$ PFU (100 $LD_{50}$) of vaccinia WR by the IN route. Survival rate over 14 days after challenge was determined. Dose-responsive protection was seen with all virus strains, and all clones protected mice at least as well as Dryvax®. There were no differences in the protective activity among the clones. The average survival times at different immunizing doses are summarized in Table 3 and the 50% protective doses ($PD_{50}$) are shown in Table 4.

TABLE 3

Survival time of immunized mice following challenge with 100 $LD_{50}$ of vaccinia WR.

| Immun. dose | Average survival time (days) | | | |
|---|---|---|---|---|
| (log10 pfu/ml) | Dryvax | Clone 3 | Clone 2 | Clone 4 |
| 8 | 14.0 | NT | 14.0 | NT |
| 7 | 14.0 | 14.0 | 14.0 | 14.0 |
| 6 | 12.0 | 14.0 | 12.4 | 12.4 |
| 5 | 7.6 | 8.8 | 7.2 | 7.0 |
| 4 | 5.2 | 5.2 | 7.8 | 5.4 |
| 3 | 5.6 | 5.4 | 5.4 | 4.8 |
| 2 | 5.2 | 5.8 | 5.2 | NT |

TABLE 4

50% protective doses of Dryvax ® and vaccine candidates.
PD50 (log10 pfu)

| Dryvax | Clone 3 | Clone 2 | Clone 4 |
| --- | --- | --- | --- |
| 5.5 | 5.2 | 5.4 | 5.5 |

Restriction Endonuclease Analysis

Figure 1A:
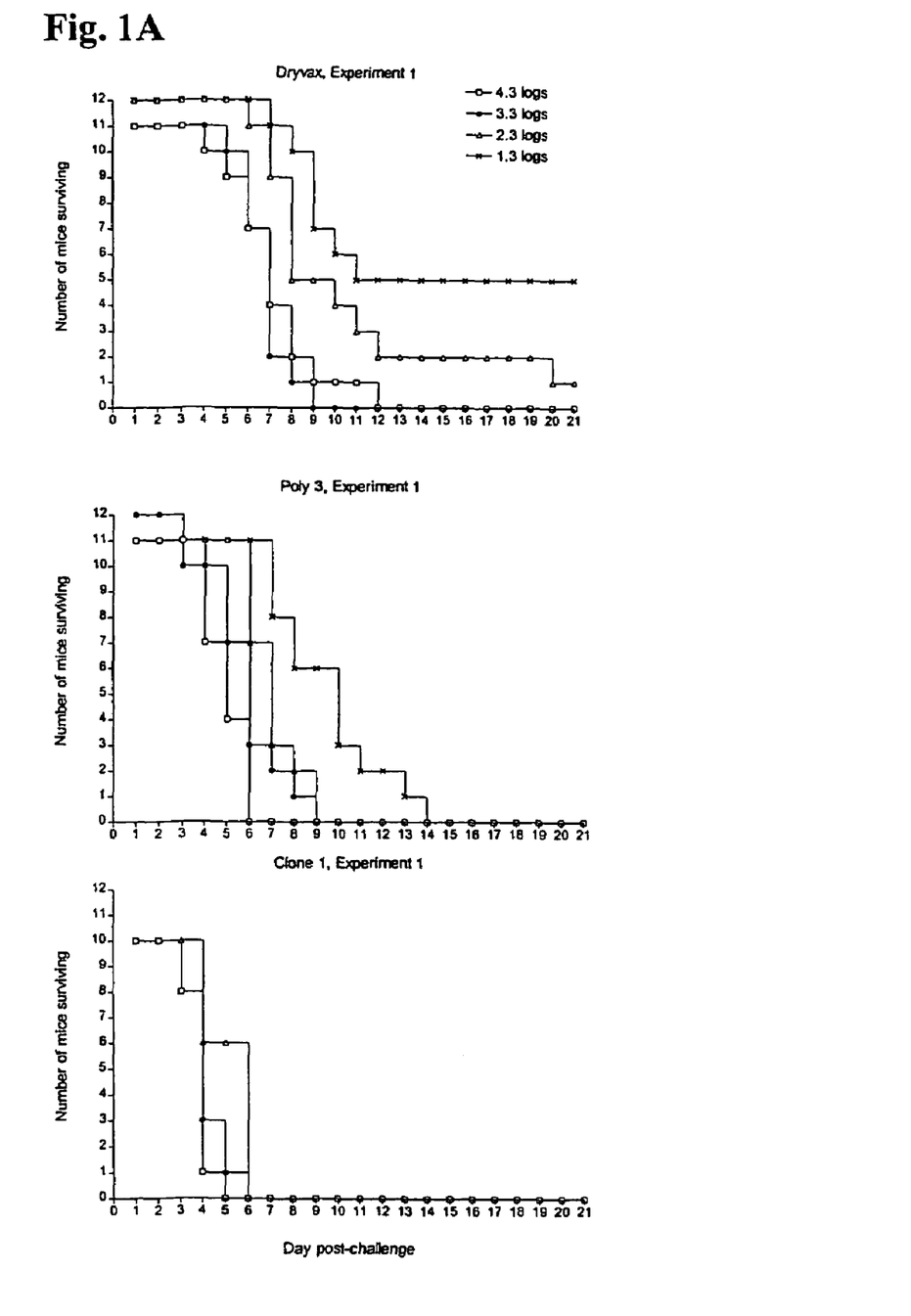
FIGS. 1A-1D are a series of graphs showing the results of experiments in which suckling mice were challenged with the indicated vaccinia clones, a polyclonal vaccinia virus preparation, or Dryvax®. The number of mice surviving and average survival time after these challenges are shown.
Figure 1B:
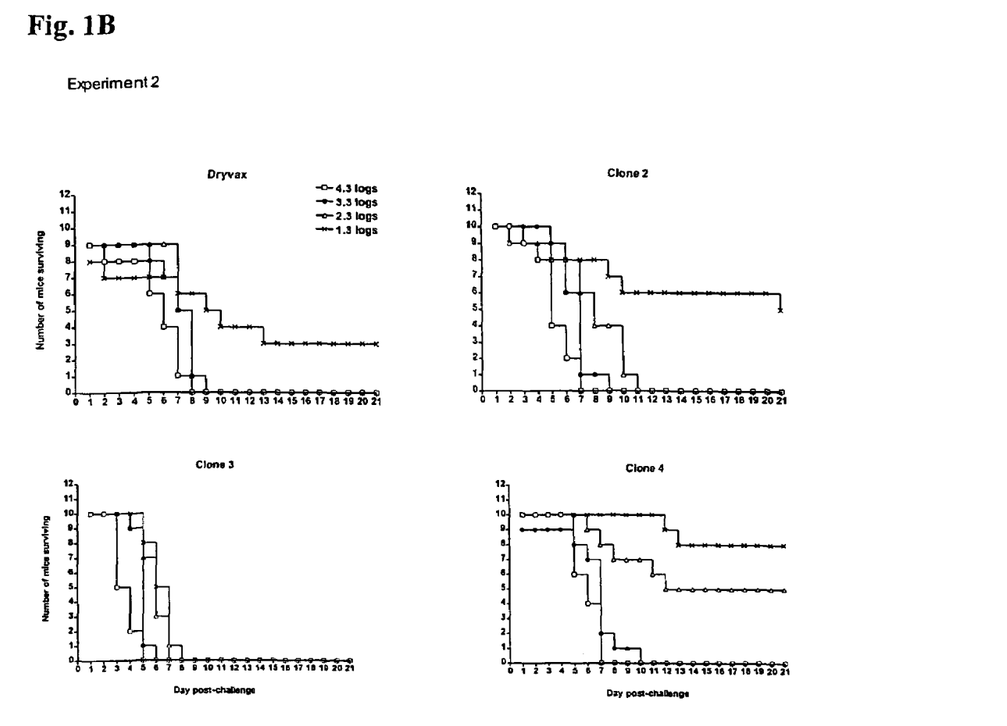
Figure 1C:
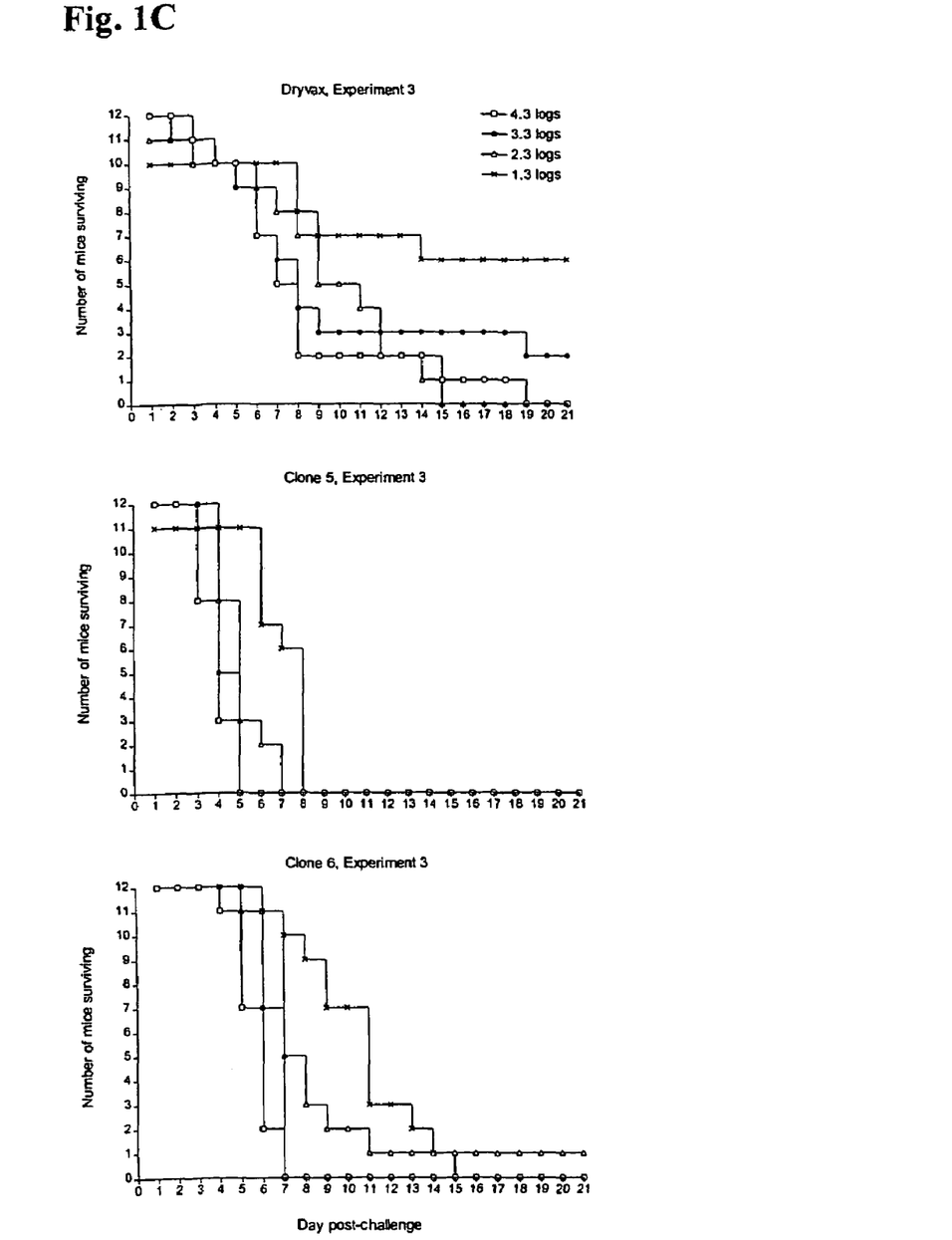
Figure 1D:
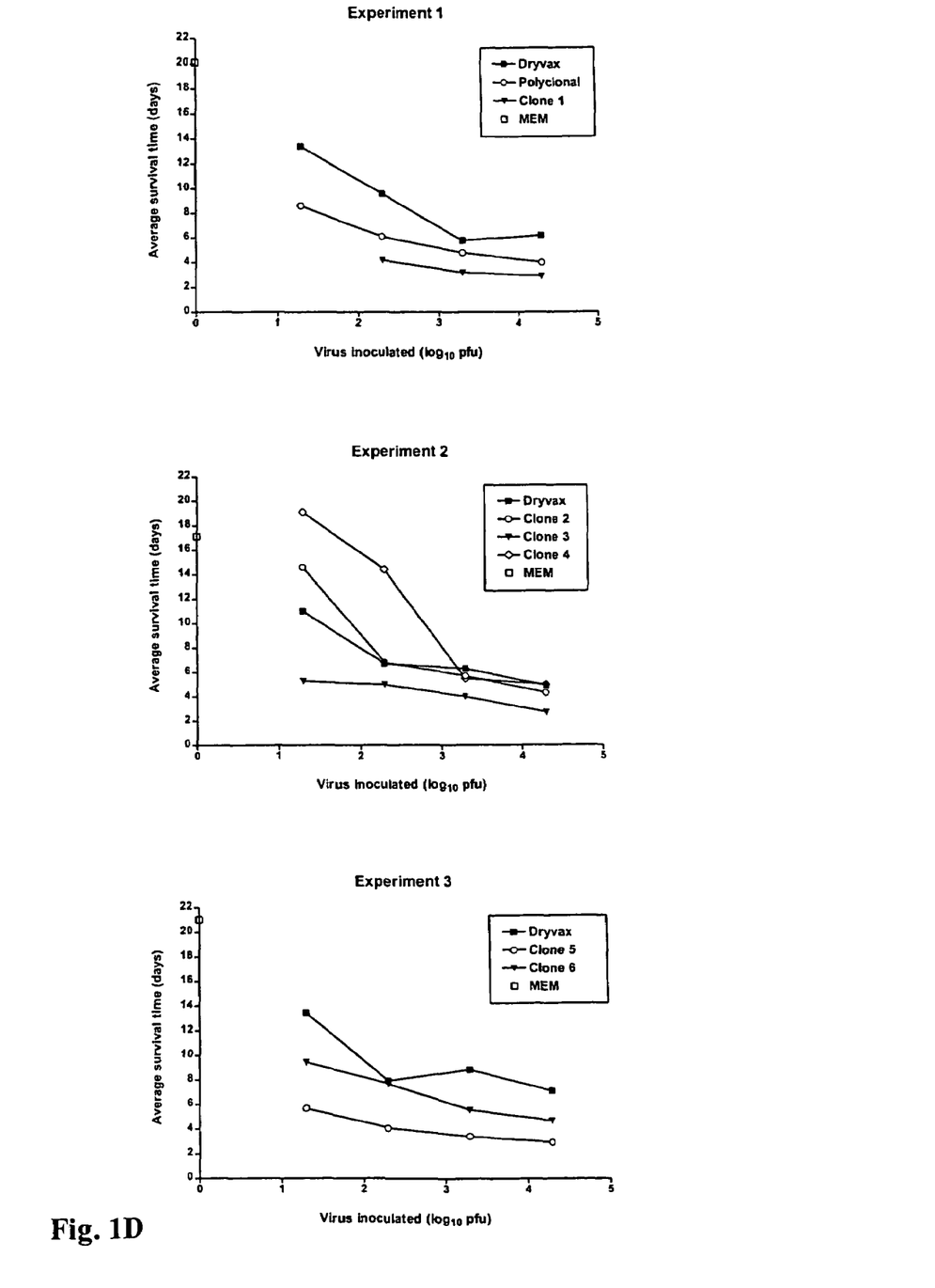
Figure 2:
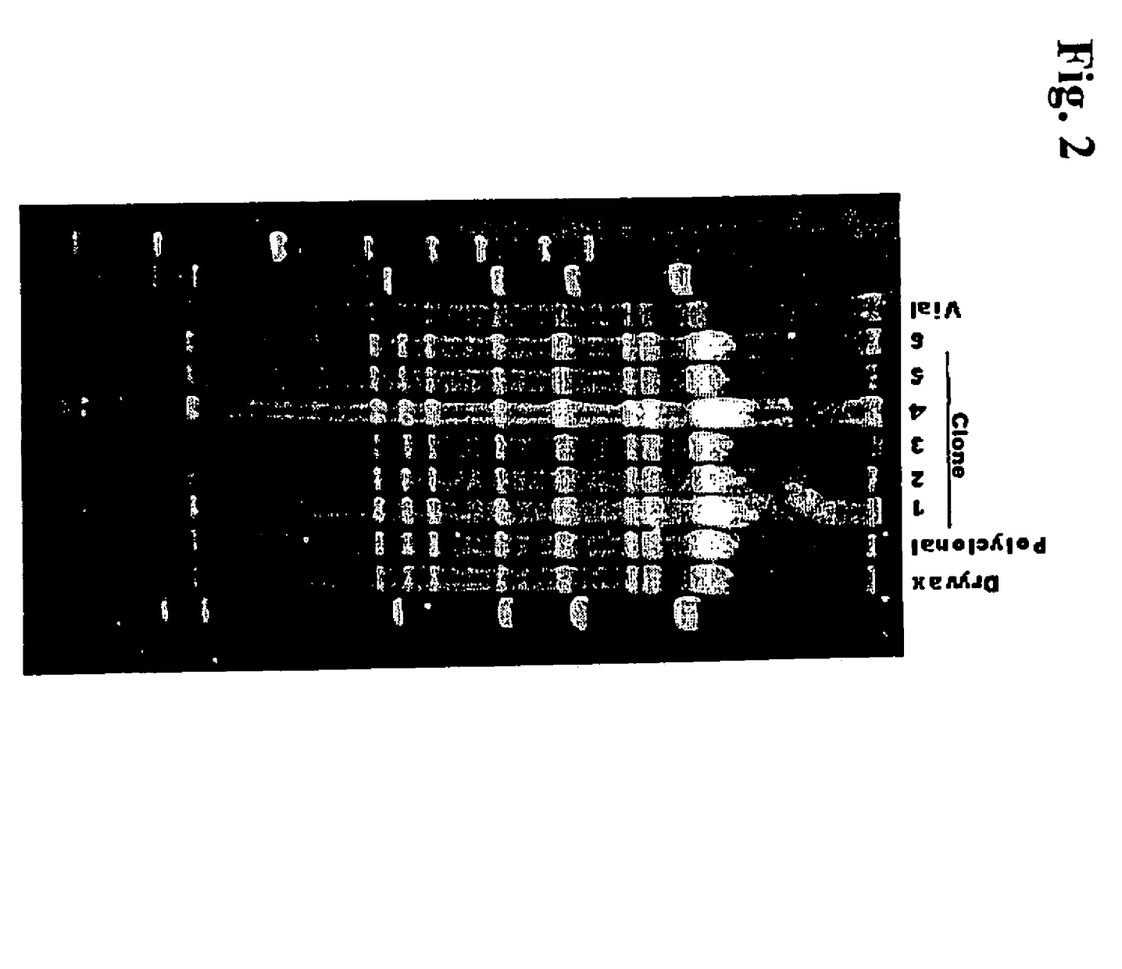
FIG. 2 shows a HindIII restriction enzyme digestion analysis of vaccine clones of the invention, as compared to a polyclonal virus preparation and Dryvax®.

DNA from Dryvax® and each vaccine candidate was purified and subjected to restriction endonuclease digestion by HindIII to determine whether there are genetic differences among the strains. No differences were detected, as is shown in the electrophoretic analysis of digested genomic DNA shown in FIG. 2.

Selection of a Cell Substrate

Studies of Dryvax® replication and yields in MRC-5 cells and primary chick embryo fibroblast (CEF) cells were undertaken, and showed yields to be lower in CEF cells than in MRC-5. MRC-5 cells were thus selected as the substrate for vaccine development. Candidates can be tested in CEF or other cells to compare vaccine yields.

Growth media for MRC-5 cell expansion were also compared. Williams E medium, Minimal Essential Medium (MEM), and Dulbecco's MEM gave equivalent results. Media enrichment with additional fetal bovine serum (FBS), nonessential amino acids, vitamins, and sodium pyruvate provided no advantages over medium with 10% FBS with respect to cell viability or growth. MRC-5 growth kinetics at appropriate cell seeding density was adequate. The cell plant density was determined to be $2\times10^4$ cells/$cm^2$. The time to split was determined to be 3-5 days, and the population doubling/split was determined to be 1-1.5. A method for producing cell banks and for cell expansion for virus growth was defined. Standard trypsinization methods were shown to be suitable for cell dissociation. An alternative method using bacterial pronase was shown to be useful, and may have the advantage of avoiding animal derived products in manufacturing.

Variants of ACAM1000/ACAM2000

The sequences of ACAM1000 and ACAM2000 are provided in SEQ ID NOs: 1 and 2, respectively. The coding sequences and corresponding protein sequences taken from the ACAM2000 sequence are provided in SEQ ID NOs:3-472 (also see the enclosed sequence appendices). Viruses that comprise these sequences, as well as compositions including them and methods employing them, are included in the present invention.

Also included in the invention are variants of these viruses, which have sequences that are similar to, but not identical to, those of the viruses. In particular, variant viruses of the invention can include nucleotide sequences that are, for example, at least 70%, 75%, 80%, 85%, 90%, 95%, 96%, 97%, 98%, or 99% (e.g., at least 99.2%, 99.5%, 99.7%, 99.8%, 99.9%, 99.95%, 99.99%, 99.995%, or 99.999%) identical to the sequences of SEQ ID NOs: 1 or 2. This level of identity can be throughout the entire sequences of the viruses, or can be within a particular region, such as, for example, any one (or more) of the coding sequences of SEQ ID NOs: 1 or 2 (or their complements). Thus, for example, any of the levels of identity noted above can be present in one or up to 235 of SEQ ID NOs:3-471 (odd numbers), in any combination.

The variant viruses can also include sequences that hybridize to the sequences of SEQ ID NOs: 1 or 2 (or their complements) under highly stringent conditions (see above). This criterion can be applied to the sequence of the variant virus as a whole, or to regions within the viral genomes, such as individual coding sequences. Thus, for example, virus variants of the present invention also include viruses that comprise one or up to 235 sequences that hybridize to the corresponding sequence in SEQ ID NOs: 1 or 2 under highly stringent conditions, in any combination.

Variant viruses of the invention can further be characterized as comprising sequences encoding one or up to 235 polypeptides of the sequences of SEQ ID NOs:4-472 (even numbers). Thus, the invention includes viruses that include sequences that are different from SEQ ID NOs: 1 or 2, but encode one or up to 235 of the same polypeptides as these sequences, due to the degeneracy of the genetic code. The variants can also include sequences that encode one or up to 235 of the polypeptides encoded by SEQ ID NOs: 1 or 2, but with conservative changes in the sequences (see above).

For all variants, it is preferable that the viruses have substantially the same virulence, immunogenicity, growth characteristics in culture, or restriction endonuclease digestion pattern as Dryvax®, ACAM1000, or ACAM2000, as discussed above. Assays for making these determinations are well known in the art, and examples are described above.

All references cited above are herein incorporated by reference. Other embodiments of the invention are within the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07645456B2). An electronic copy of the "Sequence Listing" will also be available from the USPTO upon request and payment of the fee set forth in 37 CFR 1.19(b)(3).

What is claimed is:

1. A pharmaceutical composition comprising an isolated clonal strain of attenuated vaccinia virus, wherein the isolated clonal strain of attenuated vaccinia virus is ACAM1000 (ATCC Deposit No. PTA-3321).

2. A pharmaceutical composition comprising an isolated clonal strain of attenuated vaccinia virus that is obtained from cell cultures in which ACAM1000 (ATCC Deposit No. PTA-3321) has been propagated.

* * * * *

UNITED STATES PATENT AND TRADEMARK OFFICE
CERTIFICATE OF CORRECTION

| | |
|---|---|
| PATENT NO. | : 7,645,456 B2 |
| APPLICATION NO. | : 10/826680 |
| DATED | : January 12, 2010 |
| INVENTOR(S) | : Weltzin et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 877 days.

Signed and Sealed this

Twenty-eighth Day of December, 2010

David J. Kappos
*Director of the United States Patent and Trademark Office*